United States Patent
Hansson

[19]

[11] Patent Number: 6,109,919
[45] Date of Patent: Aug. 29, 2000

[54] IMPLANT SYSTEM

[75] Inventor: Stig Hansson, Mölndal, Sweden

[73] Assignee: Astra Aktiebolag, Sodertalje, Sweden

[21] Appl. No.: 09/077,144

[22] PCT Filed: Apr. 21, 1998

[86] PCT No.: PCT/SE98/00730

§ 371 Date: May 21, 1998

§ 102(e) Date: May 21, 1998

[87] PCT Pub. No.: WO98/48729

PCT Pub. Date: Nov. 5, 1998

[30] Foreign Application Priority Data

Apr. 28, 1997 [SE] Sweden .................................. 9701582

[51] Int. Cl.[7] ........................................................ A61C 8/00
[52] U.S. Cl. ............................................ 433/173; 433/172
[58] Field of Search ...................................... 433/172, 173, 433/174, 175, 176, 201.1

[56] References Cited

U.S. PATENT DOCUMENTS

| | | |
|---|---|---|
| 4,178,686 | 12/1979 | Riess et al. ........................ 433/173 X |
| 4,185,383 | 1/1980 | Heimke et al. ........................ 433/173 |
| 4,215,986 | 8/1980 | Riess ........................................ 433/173 |
| 4,270,905 | 6/1981 | Mohammed ........................ 433/173 X |
| 5,052,930 | 10/1991 | Lodde et al. ........................... 433/173 |
| 5,092,771 | 3/1992 | Tatum, III ............................. 433/173 |
| 5,269,686 | 12/1993 | James ................................ 433/173 X |
| 5,366,374 | 11/1994 | Vlassis ............................. 433/173 X |
| 5,419,701 | 5/1995 | Propper ................................. 433/173 |
| 5,427,526 | 6/1995 | Fernandes ............................. 433/173 |
| 5,447,435 | 9/1995 | Brodbeck ............................... 433/173 |
| 5,538,427 | 7/1996 | Hoffman et al. ..................... 433/173 |
| 5,658,147 | 8/1997 | Phimmasone ..................... 433/173 X |

*Primary Examiner*—Nicholas D. Lucchesi
*Attorney, Agent, or Firm*—White & Case LLP

[57] ABSTRACT

A fixture (301) of a dental implant system for implantation in bone tissue (312, 314) of the maxilla or mandible by displacement thereof in a forward direction for supporting a superstructure such as an abutment, the fixture having a forward end, a rearward end (330) which presents an interfacing surface (350) for interfacing with an interfacing surface of the superstructure and an outer surface (305) which forwardly of a predetermined position (307) on the outer surface is adapted for interlocking with bone tissue of the maxilla or mandible. The interfacing surface of the fixture is structurally isolated from the fixture outer surface to a level which is both forwardly of the interfacing surface and the predetermined position on the fixture outer surface.

23 Claims, 6 Drawing Sheets

IMPLANT SYSTEM

The present invention relates to an implant system, specifically a dental implant system for a partially or fully edentulous patient which comprises a fixture for implantation into the bone tissue of the maxilla or mandible of the patient for supporting a superstructure which in turn supports or presents a dental restoration comprising one or more artificial replacement teeth. As an example, the superstructure may be an abutment which is adapted in use to be connected to the implanted fixture to bridge the soft tissue layer (gingiva) overlying the maxilla or mandible for a restoration structure such as a crown or bridge to be secured thereto.

In a typical dental implant system the superstructure is screw retained to the fixture. To this end, the fixture has an internally threaded socket which opens in a rear end of the fixture. The internal threads may be present throughout the socket or alternatively just in a section of the socket. The superstructure is then either (i) integrally formed with an externally threaded projection for screwing into the internally threaded socket to secure the superstructure to the fixture, or (ii) comprises a sleeve part having a lumen in which a transverse bearing surface is provided, and a screw part for passage through the lumen of the sleeve into the internally threaded socket, the screw having an enlarged head which is adapted in use to bear against the transverse bearing surface in the lumen of the sleeve thereby ensuring that the superstructure is secured to the fixture on screwing of the screw into the internally threaded socket.

In other dental implant systems the superstructure is secured to the fixture through non-screw thread connections, e.g. by cementing.

Whatever the form of securement of the superstructure to the fixture, the superstructure transmits a load to the fixture in the implantation direction through mutually interfacing surfaces.

Fixation of a fixture of a dental implant system in the bone tissue of the maxilla or mandible primarily relies upon mechanical interlocking of bone tissue to the outer surface of the fixture. Substantial interlocking between the outer surface of a fixture and the bone tissue of the maxilla or mandible occurs when the outer surface is roughened, for example by providing the fixture outer surface with screw threads, recesses, holes etc. (macroroughening), forming pits in the fixture outer surface by blasting, plasma spraying, etching, hydroxyapatite coating, the provision of beads on the outer surface etc. (microroughening) or machining the fixture outer surface. Interlocking between the outer surface of a fixture and bone tissue of the maxilla or mandible into which the fixture is implanted enables the fixture to greater withstand shear stresses. One can consider this to be due to bone tissue growing into the cavities in the fixture outer surface created by the roughening.

A macroroughened fixture outer surface produces more effective interlocking than a microroughened fixture outer surface which in turn produces more effective interlocking than a machined fixture outer surface. All, however, produce more effective interlocking than fixtures having an outer surface which is smooth, e.g. a polished outer surface. More than one form of surface roughening can be applied to a fixture to promote interlocking. For example, it is known to provide a fixture with both a macro- and a microroughened outer surface.

In 1892 it was suggested by J. Wolff (*Das Gesetz der Transformation der Knochen. Berlin: A. Hirschald*, 1892) that bone tissue remodels itself in response to the mechanical loading history of the bone and in accordance with mathematical laws. This has since proved to be correct and is therefore now known as Wolff's law. Some consequences of Wolff's law are that:

1. If the stresses or strains to which bone tissue is exposed are lowered a net loss of bone tissue (bone resorption) will result until a new steady state is obtained where the stresses or strains are normal.
2. If the stresses or strains to which bone tissue is exposed are normal then no net change to the bone tissue will result.
3. If the stresses or strains to which bone tissue is exposed are increased within physiological limits bone tissue build up will result until a new steady state is obtained where the stresses or strains are normal.
4. If the stresses or strains to which bone tissue is exposed are extremely high then bone resorption will result.

Wolff's law thus indicates the need for stress conditions in the bone tissue adjacent an implant fixture which are favourable for the maintenance of a steady state in the bone tissue. Otherwise, marginal bone resorption will result which will cause destabilisation of the osseointegration of the fixture with the bone tissue and a reduction in the aesthetic appeal of the dental implant system when implanted, an important commercial consideration.

With this in mind, the Applicant's have identified an interdependence between the stress conditions in the bone tissue adjacent an implant fixture and the manner in which a superstructure interfaces with the fixture in the implantation direction vis-à-vis the level on the fixture outer surface where interlocking starts. The present invention takes account of this interdependence to help improve the stress conditions in the bone tissue adjacent the outer surface of an implanted fixture.

According to the invention there is provided a fixture for implantation in bone tissue of the maxilla or mandible by displacement thereof in a forward direction for supporting a superstructure, the fixture having a forward end, a rearward end which presents an interfacing surface for interfacing with an interfacing surface of the superstructure, and an outer surface which forwardly of a predetermined position on the outer surface is adapted for interlocking with bone tissue of the maxilla or mandible, characterised in that the interfacing surface of the fixture is structurally isolated from the fixture outer surface to a level which is both forwardly of the interfacing surface of the fixture and the predetermined position on the fixture outer surface.

This interfacial arrangement results in an improved stress distribution in the adjacent bone tissue of the maxilla or mandible. For example, the peak interfacial shear stress is shifted forwardly where the risk of triggering off stress induced bone resorption is less. Moreover, a lower peak interfacial shear stress value is generally obtained. In addition, the longitudinal compressive stresses (relative to the maxilla or mandible ridge) in the bone tissue and the stresses caused by the horizontal loads or bending moments on the fixture are less as one moves more forwardly into the bone tissue and therefore the peak interfacial shear stress generated in the bone tissue can be more easily accommodated there.

In an embodiment of the invention the interfacing surface of the fixture is at a level disposed at, or rearwardly of, the predetermined position on the outer surface.

In an embodiment of the invention hereinafter to be described the interfacing surface is a land at the rearward end of the fixture which is structurally isolated from the outer surface by an endless recess at the rearward end which surrounds the land, the recess having a base positioned forwardly of the predetermined position on the fixture outer surface and the land being disposed at a level rearward of said base. The endless recess can take on a variety of cross-sectional shapes, e.g. annular.

In an embodiment of the invention the recess has endless inner and outer rearward edges and the land is disposed at a level which is coincident with, forward of, or rearward of the endless outer rearward edge.

In an embodiment of the invention the land is disposed at a level coincident with the endless inner rearward edge of the recess.

In an embodiment of the invention the superstructure and fixture only interface through the interfacing surfaces.

In an embodiment of the invention at least a section of the outer surface of the fixture is roughened for interlocking with the bone tissue, the at least a section of the outer surface having a rearward edge and a forward edge, and the predetermined position on the outer surface is defined by the rearward edge or a position intermediate the rearward and forward edges. The latter example would be the case where the rearward edge projects from the maxilla or mandible on implantation of the fixture. The roughening may be achieved by macroroughening, e.g. by the provision of screw threads, recesses, holes etc., or by microroughening through blasting, plasma spraying, etching, hydroxyapatite coating, the provision of beads on the outer surface etc. or a mixture of both. The roughening can also be achieved by machining.

The more rearward the predetermined position or attachment level is disposed on the fixture outer surface the more bone tissue is involved in the load carrying. Finite element analysis also indicates that the more rearward the attachment level is disposed on the fixture outer surface the less the peak interfacial shear stress value. A rearwardly disposed attachment level is thus preferable and accordingly in an embodiment of the invention at least a forward section of the fixture which presents the forward end is adapted in use to be inserted into bone tissue for implantation of the fixture, the at least a forward section has a rearward edge and the predetermined position on the fixture outer surface is disposed at the rearward edge of the at least a forward section whereby the predetermined position on the fixture outer surface registers or substantially registers with the outer surface of the maxilla or mandible when the fixture is implanted.

Preferably, the fixture outer surface is adapted to interlock with the bone tissue between the predetermined position on the fixture outer surface and the forward end of the fixture. The predetermined position on the fixture outer surface may coincide with the rearward edge of the fixture outer surface.

In an embodiment of the invention hereinafter to be described the interfacing surfaces of the fixture and superstructure are unthreaded surfaces.

In an embodiment of the invention the fixture is an endosteal fixture of root form. By "root form" is meant that the fixture has a generally cylindrical shaft which in use of the fixture is implanted in the bone tissue of the maxilla or mandible. The outer surface of the shaft is roughened for interlocking with the bone tissue, e.g. the shaft may be in the form of a screw. The term "root form" is used to distinguish the fixture from endosteal blade fixtures. The differences between theses two forms of endosteal fixture is shown in *Biomaterials Science: An Introduction to Materials in Medicine*, Ratner, Buddy D. et al, Chapter 7.4, Academic Press, 1996.

The present invention further provides a dental implant system comprising a fixture according to the invention and a superstructure for mounting on the fixture, the superstructure having a forward end which presents an interfacing surface for interfacing with the interfacing surface of the fixture in the forward direction.

The invention yet further provides a method of installing a dental restoration in the oral cavity of a patient comprising the steps of:

providing a fixture having an outer surface at least a section of which is adapted for interlocking with bone tissue of the maxilla or mandible;

providing a superstructure on which the dental restoration is formed or mountable;

implanting the fixture in the maxilla or mandible of the patient in a forward direction such that at least a forward part of the at least a section of the outer surface is disposed adjacent the bone tissue of the maxilla or mandible; and mounting the superstructure on the fixture such that the superstructure interfaces with the fixture in the forward direction on an interfacing surface of the fixture which is structurally isolated from the fixture outer surface to a level which is both forward of the interfacing surface of the fixture and the position at which interlocking between the fixture outer surface and bone tissue commences.

The superstructure may take the form of an abutment for bridging the soft tissue layer overlying the maxilla or mandible.

By way of example, embodiments of the present invention will now be described with reference to the accompanying Figures of drawings in which:

FIG. 5A is a schematic view of a prior art dental implant system comprising a fixture having a rearward end which when the fixture is implanted projects rearward of the outer surface of the bone tissue of the maxilla or mandible and in which there is provided a female recess and further having an interlocking outer surface with an attachment level which starts at the entry point of the fixture in the bone tissue when implanted, and an abutment for bridging the soft tissue layer overlying the maxilla or mandible to support a restoration having a male projection at the forward end thereof which is so constructed and dimensioned vis-à-vis the female recess that the fixture and abutment interface such that the fixture is loaded in the implantation direction through interfacing surfaces which are disposed rearward of the attachment level.

In the Figures of drawings like numerals indicate like parts.

Figure 1:
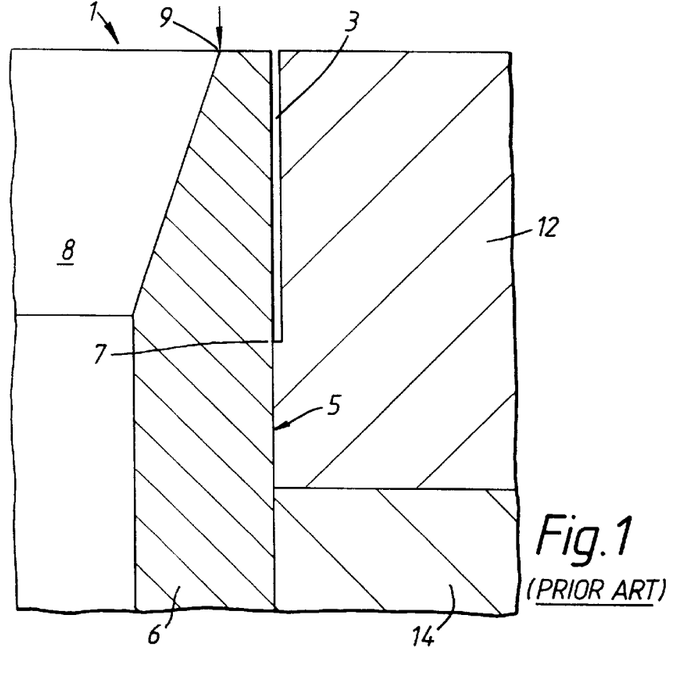
FIG. 1 is a sectional view of a part of a rear end of a fixture of a prior art dental implant system implanted in the bone tissue of a maxilla or mandible in which the outer surface of the fixture comprises a smooth rearward section and an interlocking forward section and to which a superstructure of the system interfaces therewith such that it applies a load to the fixture in the implantation direction through interfacing surfaces disposed rearward of the interlocking forward section of the outer surface.

In FIG. 1 there is shown a sectional view of a part of a rear end of a root form endosteal fixture 1 of a prior dental implant system implanted in the maxilla or mandible with an extent which encompasses both cortical bone tissue 12 and cancellous bone tissue 14. The fixture 1 has a body 6 which presents the outer surface of the fixture 1 which faces the bone tissue 12, 14 and in which a socket 8 extends forwardly from an opening in the rear end of the fixture 1 to a position intermediate the rear end and a forward end of the fixture 1 for use in connecting a superstructure (not shown) such as an abutment to the rear end of the fixture 1.

The outer surface of the fixture 1 is split into a smooth rearward section 3 adjacent the cortical bone 12 and an interlocking screw threaded forward section 5 having an axial extent which encompasses both the cortical and cancellous bone tissue 12, 14. Substantial interlocking between the fixture outer surface and surrounding bone tissue 12, 14 thus starts at a level 7 (the "attachment level") which is disposed at a level below or forward of the entrance point of the fixture 1 into the bone tissue 12, 14.

In this dental implant system the superstructure presents an unthreaded interfacing surface which interfaces with the fixture 1 on an unthreaded edge surface 9 of the socket 8. The implanted fixture 1 is thus loaded in the implantation or forward direction by the superstructure well above or rearward of the attachment level 7, as indicated by the arrow in FIG. 1.

Figure 2:
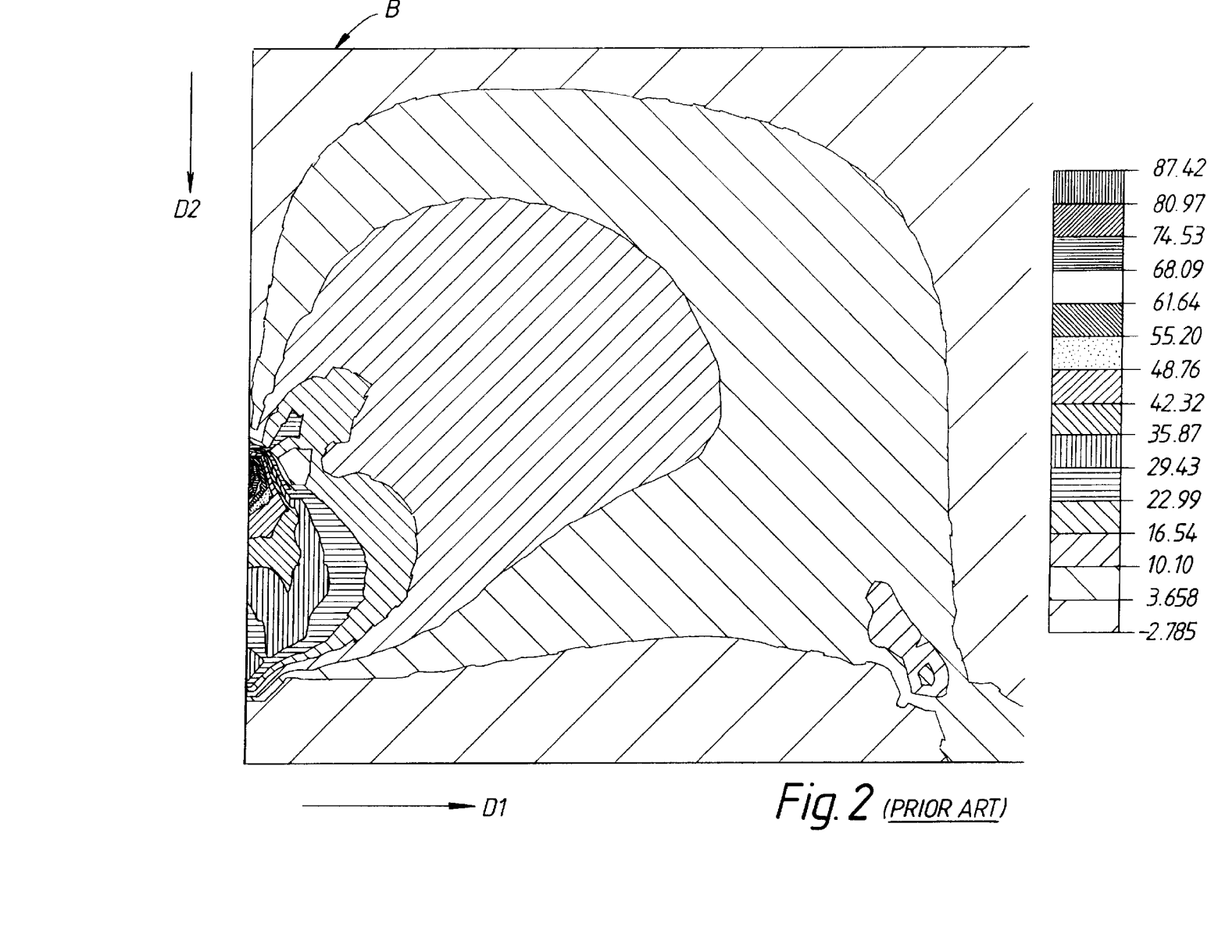
FIG. 2 is a finite element analysis of the stress distribution in the bone tissue adjacent the fixture of FIG. 1 when the superstructure interfaces with the fixture with a load of 1000N being applied to the fixture in the implantation direction through the interfacing surfaces.

FIG. 2 is a finite element analysis of the stress distribution resulting in the bone tissue adjacent the fixture 1 of the dental implant system of FIG. 1 when a forwardly directed load of 1000N is applied to the fixture 1 on the edge surface 9. The x axis in the analysis indicates the distance from the fixture outer surface D1 while the y axis indicates the distance into the bone tissue D2 from the bone tissue surface B. The vertical bar chart on the right hand side is the key for the stresses (MPa) represented in the analysis.

As can be seen from FIG. 2, a relatively high interfacial shear stress peak occurs in the bone tissue of the maxilla or mandible adjacent the fixture 1 at or just below the attachment level 7. The finite element analysis also reveals that a very low stress is experienced in the bone tissue adjacent the smooth rearward outer surface section 3. Consideration of Wolff's law helps to explain why marginal bone resorption is in practice observed around the rearward section 3, namely because the interfacial engagement of the superstructure and the fixture 1 leads to stress conditions in the bone tissue adjacent the smooth rearward outer surface section 3 and the attachment level 7 which are unfavourable for the maintenance of a steady state in the bone tissue.

Figure 3:
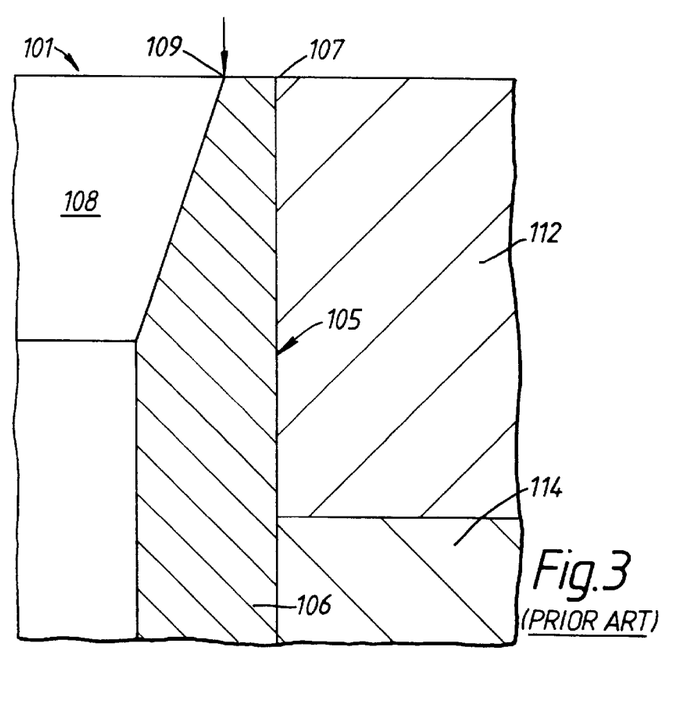
FIG. 3 is a sectional view of a part of a rear end of another fixture of a prior art dental implant system implanted in the bone tissue of a maxilla or mandible having an interlocking outer surface with an attachment level coincident with the fixture entry point into the bone tissue and to which a superstructure of the system interfaces therewith such that it applies a load to the fixture in the implantation direction through interfacing surfaces disposed coincident with the attachment level.

In FIG. 3 there is shown the interfacial loading and bone tissue interlocking conditions for a root form endosteal fixture 101 of another hitherto proposed dental implant system. The fixture 101 is provided with an interlocking machined outer surface 105 with an attachment level 107 which starts where the fixture 101 enters the bone tissue and the superstructure (not shown) has an unthreaded surface which interfaces with an unthreaded edge surface 109 of the socket 108 of the fixture 101 which is at a corresponding level to the attachment level 107. Loading of the fixture 101 in the implantation or forward direction thus also occurs at the level of the attachment level 107.

Figure 4:
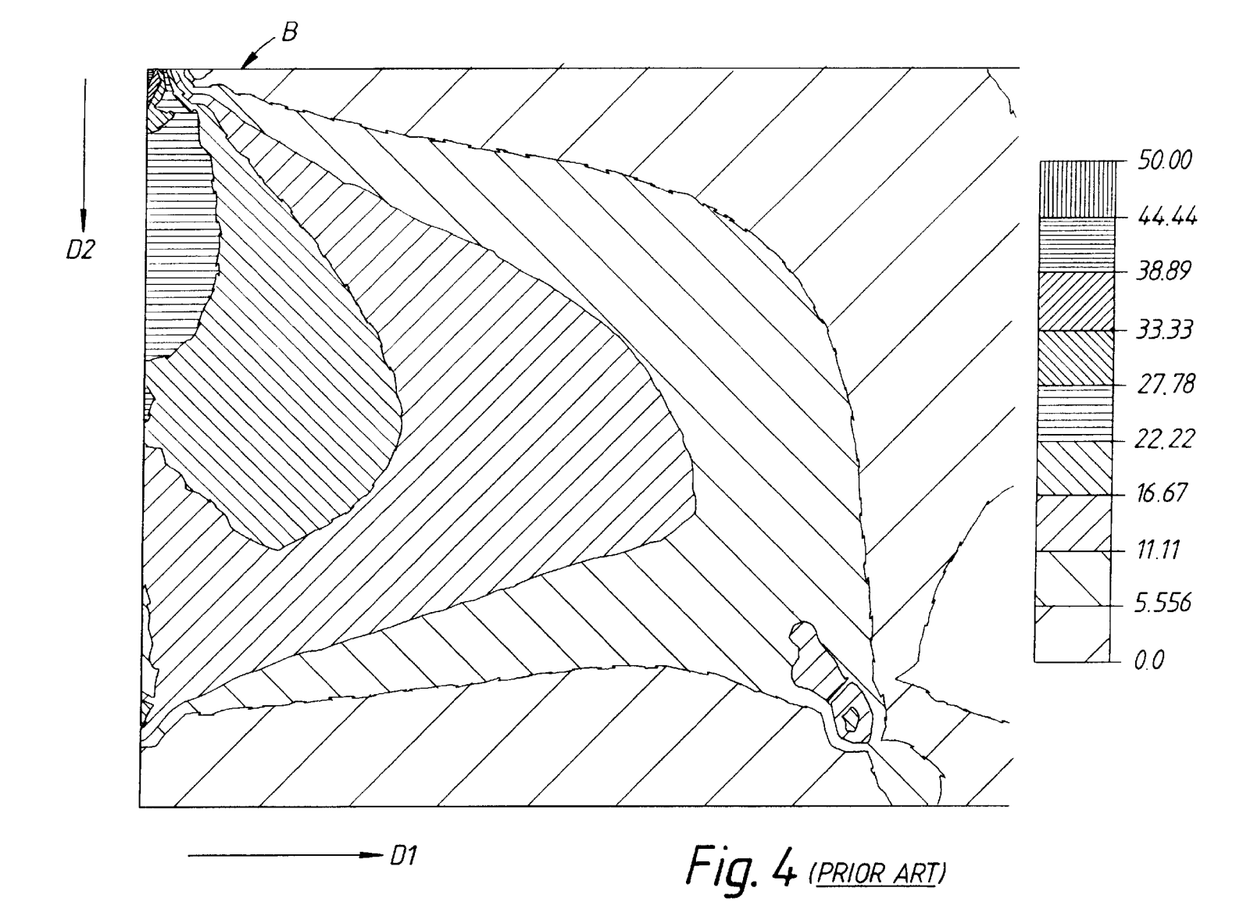
FIG. 4 is a finite element analysis of the stress distribution in the bone tissue adjacent the fixture of FIG. 3 when the superstructure interfaces with the fixture with a load of 1000N being applied to the fixture in the implantation direction through the interfacing surfaces.

A finite element analysis of the stress distribution resulting in the bone tissue adjacent the fixture 101 of the dental implant system of FIG. 3 when a forwardly directed load of 1000N is applied to the fixture 101 on the edge surface 109 is shown in FIG. 4. The maximum interfacial shear stress still coincides with the attachment level 107 although it is reduced as compared to the FIG. 1 system where the attachment level is disposed more forwardly on the fixture outer surface. In addition, all of the coronal cortex is able to support the load of the superstructure in this arrangement. The risk of marginal bone resorption due to disuse hypotrophy is thus reduced for this arrangement.

However, the peak interfacial shear stress is still very high. Moreover, the peak interfacial shear stress in the bone tissue is unfavourably positioned just below the fixture entry point into the bone tissue. This positioning of the peak interfacial shear stress is unfavourable because the entrance point of the fixture 101 into the bone tissue is sensitive due to mild inflammatory processes resulting from surgical trauma.

Figure 5A:
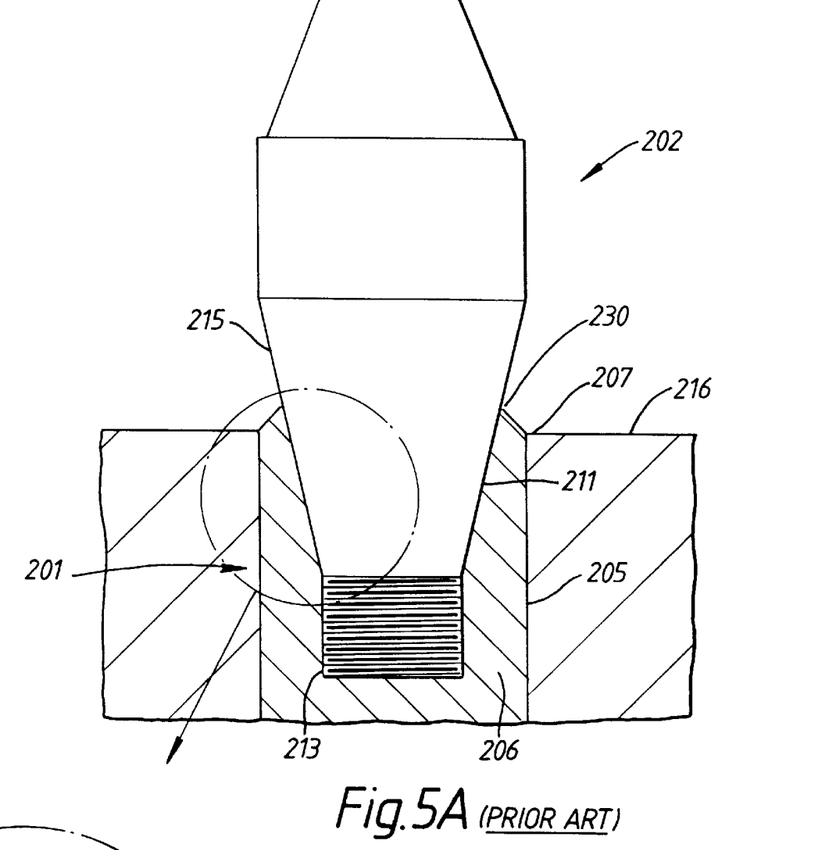
FIG. 5B is an exploded view of the interfacial contact between the fixture and abutment of FIG. 5A.
Figure 5B:
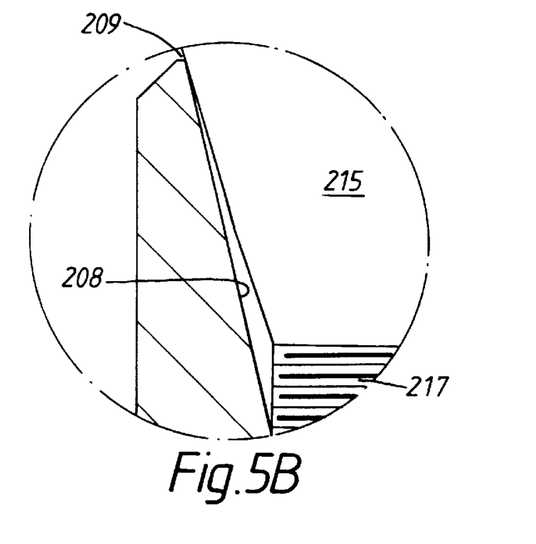

FIGS. 5A and 5B illustrate a root form endosteal fixture 201 and an abutment 202 of a further prior art dental implant system. The fixture 201 of the system is provided with a socket 208 in a rearward end 230 having a conical unthreaded rearward portion 211 and internally threaded forward portion 213 for a projection at the forward end of the abutment 202 having an unthreaded conical rearward portion 215 and an externally threaded forward portion 217 to interface with for engagement of the abutment 202 to the fixture 201. The fixture 201 is further provided with an interlocking outer surface 205 with an attachment level 207 which starts where the fixture 201 enters the bone tissue.

As shown more clearly in FIG. 5B, the angles of the flank surfaces of the conical rearward portions 211, 215 of the socket 208 and projection are such that the conical rearward portion 215 interfaces with an edge surface 209 of the conical rearward portion 211 at the open end of the socket 208 which is at a level rearward of both the attachment level 207 and the bone tissue outer surface 216.

It is to be noted that the abutment 202 could also be in the form of an abutment assembly comprising a sleeve part having at the forward end thereof the conical portion 215 and a screw part which passes through the sleeve part to present the screw thread forward portion 217.

Figure 6:
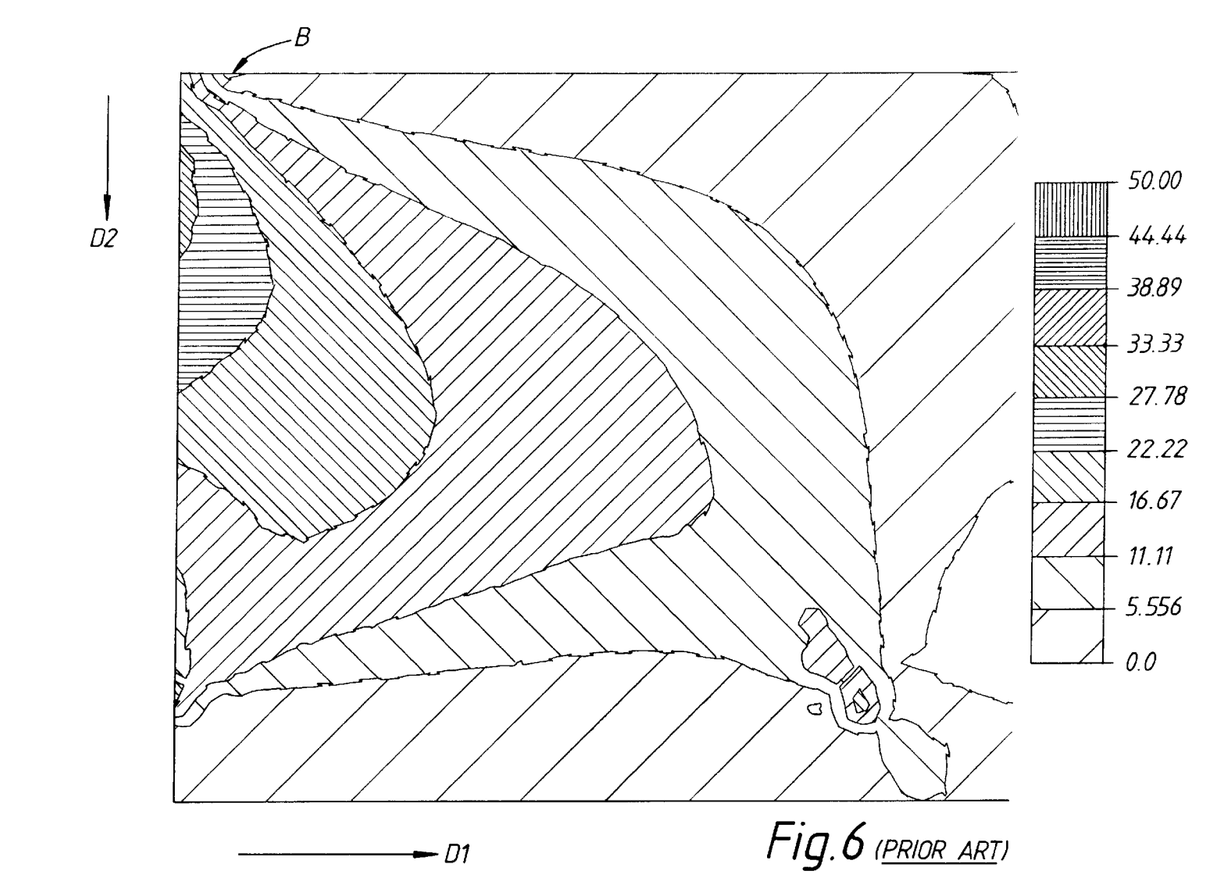
FIG. 6 is a finite element analysis of the stress distribution in the bone tissue adjacent the fixture of FIGS. 5A and 5B when the abutment interfaces with the fixture with a load of 1000N being applied to the fixture in the implantation direction through the interfacing surfaces.

A finite element analysis of the stress distribution resulting in the bone tissue adjacent the fixture 201 of the dental implant system of FIGS. 5A and 5B when a forwardly directed load of 1000N is applied to the fixture 201 on the interface surface 209 by the abutment 202 is shown in FIG. 6. The interface of the fixture 201 and abutment 202 in this system results in a reduction of the peak stress in the bone tissue around the fixture 201 under a loading of 1000N and a shifting of the peak interfacial shear stress slightly forwardly of the attachment level 207 as compared to the prior art systems previously described hereinabove with reference to FIGS. 1 to 4. The peak interfacial shear stress is still located proximate the attachment level 207, though, and thus the entrance point of the fixture 201 into the bone tissue 216.

Figure 7:
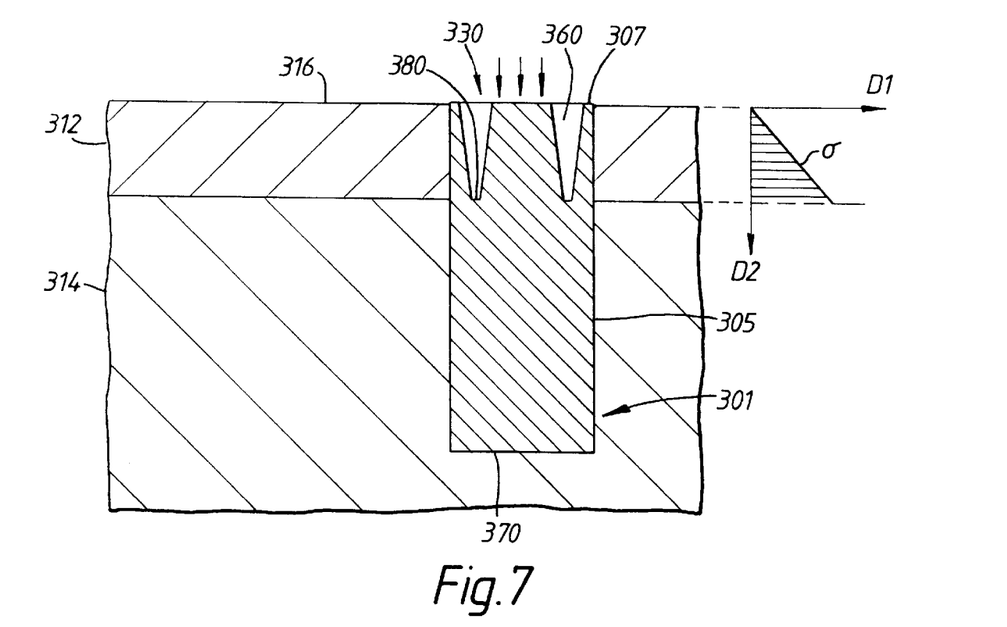
FIG. 7 is a sectional view of a fixture of a dental implant system in accordance with the invention implanted in the bone tissue of a maxilla or mandible having an interlocking outer surface with an attachment level coincident with the fixture entry point into the bone tissue and to which a superstructure of the system is adapted to interface with an interfacing surface of the fixture which is structurally isolated from the fixture outer surface to a level both forward of the interfacing surface of the fixture and the attachment level.
Figure 8:
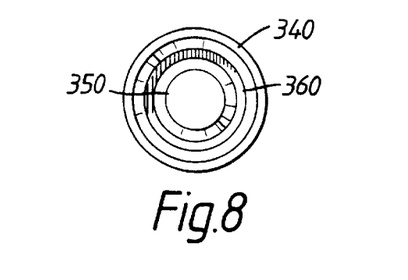
FIG. 8 is a plan view of the fixture of FIG. 7.

In FIGS. 7 and 8 there is shown a cylindrical root form endosteal fixture 301 in accordance with the present invention implanted in the bone tissue 312, 314 of the maxilla or mandible having a rearward end 330 which essentially coincides with the bone tissue outer surface 316, a forward end 370 and an interlocking outer surface 305 with an attachment level 307 at the rearward end 330 of the fixture 301. The interlocking surface 305 can be defined by macroroughening, microroughening or machining or a combination of any one of these surface features. In the rearward end 330 of the fixture 301 an annular recess 360 is provided which extends forwardly from the rearward end 330 to a base 380 disposed at a position or level which is forward of the attachment level 307, in this case to a level coincident with the transition between the cortical bone layer 312 and the cancellous bone layer 314. The rearward end 330 thus presents an annular outer surface 340 and an inner surface 350 spaced from the annular outer surface 340 by the annular recess 360.

The forward end of an abutment (not shown) of the system of which the fixture 301 forms a component part is so constructed and dimensioned that the abutment interfaces with the fixture 301 in the forward direction at least on the inner surface 350 presented at the rearward end 330 of the fixture 301. As shown by the stress distribution graph in FIG. 7 to the right of the fixture 301, this arrangement results in the peak interfacial shear stress σ in the bone tissue 312, 314 of the maxilla or mandible adjacent the fixture outer surface 305 being located well forward of both the attachment level 307 and the fixture entry point into the bone tissue 312, 314 of the maxilla or mandible. This is as a result of the recess 360 structurally isolating the inner surface 350 from the fixture outer surface 305 to a level forward of the attachment level 307 thus inhibiting or preventing the forwardly directed load applied to the inner surface 350 by the abutment being transmitted to the bone tissue 312 adjacent the fixture outer surface rearward of the base 380 of the recess 360 since there is no direct transmission path through the fixture 301 to that section of the fixture outer surface. This would also be true if the inner surface 350 was above the attachment level 307 by having the inner surface 350 above the bone tissue surface 316 as this would not affect the fact that this load carrying surface of the fixture is structurally isolated from the fixture outer surface to a position forwardly of the attachment level 307.

Furthermore, in accordance with the present invention the inner surface 350 can be located at a more forward level than shown, that is to say, forward of the attachment level 307. An improved stress distribution in the bone tissue adjacent the fixture 301 will still result as compared to the prior art systems hitherto described with reference to FIGS. 1 to 6 since finite element analysis indicates that the more forward a superstructure can apply the forwardly directed load to a fixture relative to the attachment level the more the peak interfacial shear stress in the bone tissue is reduced and shifted away from the bone tissue surface 316.

The abutment may have an annular projection at the forward end thereof for seating in the recess 360 in the fixture 301. Preferably, the projection is adapted to interface solely with the innermost boundary wall of the recess 360 because the abutment will be applying a forwardly directed load to a surface of the fixture which is not only below the attachment level 307 but which is further structurally isolated from the fixture outer surface to a level forward of the recess base 380. An improved stress distribution in the bone tissue adjacent the fixture 301 would still result even if the abutment was adapted to interface with the outermost boundary wall of the recess 360 as well as, or instead of, the innermost boundary wall of the recess 360. Alternately, the abutment does not interface in the recess 360 at all.

The inner surface 350 may be provided with a forwardly directed internally-threaded bore for a screw projection of the abutment to screw into to screw retain the abutment to the fixture 301. The screw may be an integrally formed part of the abutment or a component of a multi-part abutment as is known in the art.

The components of the dental implant system can be made from the conventional materials in the art, e.g. commercially pure titanium and alloys thereof, and by conventional methods.

In summary, the present invention provides a fixture of a dental implant system having an interlocking outer surface around which the stress distribution when implanted and mounted by a superstructure is enhanced by adapting the interfacial contact between the fixture and superstructure such that the superstructure interfaces with the fixture on an interfacing surface thereof which is structurally isolated from the fixture outer surface to a level which is both forward of the interfacing surface of the fixture and the attachment level.

What is claimed is:

1. A fixture of a dental implant system for implantation in bone tissue of the maxilla or mandible by displacement thereof in a forward direction in the maxilla or mandible for supporting a superstructure, the fixture comprising:
   a forward end,
   a rearward end which presents an interfacing surface for interfacing with an interfacing surface of the superstructure, and
   an outer surface which forwardly of a predetermined position on the outer surface is adapted for interlocking with bone tissue of the maxilla or mandible,
   wherein the predetermined position is provided at the level where interlocking between the fixture outer surface and bone tissue commences, and the interfacing surface of the fixture is structurally isolated from the fixture outer surface to a level which is both forwardly of the interfacing surface and the predetermined position on the outer surface.

2. The fixture according to claim 1, wherein the interfacing surface of the fixture is at a level disposed at, or rearwardly of, the predetermined position on the outer surface.

3. The fixture according to claim 1 or 2, wherein the interfacing surface is a land at the rearward end of the fixture which is structurally isolated from the outer surface by an endless recess at the rearward end which surrounds the land, and wherein the recess has a base positioned forwardly of the predetermined position on the fixture outer surface and the land is disposed at a level rearward of the base.

4. The fixture according to claim 3, wherein the recess has endless inner and outer rearward edges and the land is disposed at a level which is coincident with, forward of, or rearward of the endless outer rearward edge.

5. The fixture according to claim 4, wherein the land is disposed at a level coincident with the endless inner rearward edge of the recess.

6. The fixture according to claim 1, wherein at least a section of the outer surface of the fixture is roughened for interlocking with the bone tissue, and wherein the roughened section of the outer surface has a rearward edge and a forward edge, and the predetermined position on the outer surface is defined by the rearward edge or a position intermediate the rearward and forward edges.

7. The fixture according to claim 6, wherein the roughened section of the fixture outer surface is macroroughened.

8. The fixture according to claim 6 or 7, wherein the roughened section of the fixture outer surface is microroughened.

9. The fixture according to claim 6, wherein the roughened section of the fixture outer surface is roughened by machining of the section.

10. The fixture according to claim 1, wherein at least a forward section of the fixture which presents the forward end is adapted in use to be inserted into bone tissue for implantation of the fixture, the at least a forward section has a rearward edge and the predetermined position on the fixture outer surface is disposed at the rearward edge of the at least a forward section whereby the predetermined position on the fixture outer surface registers or substantially registers with the outer surface of the maxilla or mandible when the fixture is implanted.

11. The fixture according to claim 1, wherein all or substantially all of the fixture outer surface is adapted to interlock with the bone tissue between the predetermined position on the fixture outer surface and the forward end of the fixture.

12. The fixture according to claim 1, wherein the predetermined position on the fixture outer surface coincides with the rearward edge of the fixture outer surface.

13. The fixture according to claim 1, wherein the interfacing surface of the fixture is an unthreaded surface.

14. The fixture according to claim 1, wherein the fixture is an endosteal fixture of root form.

15. A dental implant system comprising a fixture for implantation in bone tissue of the maxilla or mandible by displacement thereof in a forward direction according to claim 1 and a superstructure for mounting on the fixture, wherein the superstructure has a forward end which presents an interfacing surface for interfacing with the interfacing surface of the fixture in the forward direction.

16. The system according to claim 15, wherein the superstructure takes the form of an abutment for bridging the soft tissue layer overlying the maxilla or mandible.

17. The system according to claim 15 or 16, wherein the interfacing surfaces of the fixture and superstructure are unthreaded surfaces.

18. The system according to claim 15, wherein the interfacing surfaces of the fixture and superstructure are the only interfacing surfaces.

19. A method of installing a dental restoration in the oral cavity of a patient comprising the steps of:

providing a fixture comprising an outer surface having at least a section which is adapted for interlocking with bone tissue of the maxilla or mandible;

providing a superstructure on which the dental restoration is formed or mountable;

implanting the fixture in the maxilla or mandible of the patient by displacement thereof in a forward direction in the maxilla or mandible such that at least a forward part of the at least a section of the outer surface is disposed adjacent the bone tissue of the maxilla or mandible; and mounting the superstructure on the fixture such that the superstructure interfaces with the fixture in the forward direction on an interfacing surface of the fixture which is structurally isolated from the fixture outer surface to a level which is both forward of the interfacing surface of the fixture and a position on the outer surface of the fixture at which interlocking between the fixture outer surface and bone commences.

20. The method according to claim 19, wherein the interfacing surface of the fixture is disposed at a level which is at, or rearward of, the position at which interlocking between the fixture outer surface and bone tissue commences.

21. The method according to claim 19 or 20 further comprising the step of implanting the fixture such that the at least a section of the fixture outer surface is disposed adjacent bone tissue of the maxilla or mandible.

22. The method according to claim 19 further comprising the step of implanting the fixture such that interlocking between bone tissue of the maxilla or mandible and the fixture outer surface commences at the surface of the maxilla or mandible.

23. The method according to claim 19, wherein the interfacing surface of the fixture is disposed rearward of the surface of the maxilla or mandible.

\* \* \* \* \*